United States Patent [19]

Shum et al.

[11] Patent Number: 4,607,122

[45] Date of Patent: Aug. 19, 1986

[54] HIGH SELECTIVITY PROCESS FOR VAPOR PHASE OXYDEHYDROGENATION OF ALKANOIC ACIDS, SUCH AS ISOBUTYRIC ACID, USING DAWSON STRUCTURE PHOSPHOMOLYBDIC ACID

[75] Inventors: Wilfred P. Shum, East Windsor; John F. White, Princeton, both of N.J.; Eva M. Beals, Washington Crossing, Pa.

[73] Assignee: Atlantic Richfield Company, Los Angeles, Calif.

[21] Appl. No.: 258,101

[22] Filed: Apr. 27, 1981

[51] Int. Cl.[4] .................... C07C 51/14; C07C 57/02
[52] U.S. Cl. ................... 562/599; 260/405.5; 560/214
[58] Field of Search ............. 562/599; 260/405.5; 560/214

[56] References Cited

FOREIGN PATENT DOCUMENTS 52-39622  3/1977  Japan ................................. 562/599

Primary Examiner—Werren B. Lone
Attorney, Agent, or Firm—Michael S. Jarosz

[57] ABSTRACT

A novel method of converting alkanoic acids, such as isobutyric acid, to alpha-beta unsaturated acids, such as methacrylic acid, is disclosed which exhibits a higher degree of selectivity than those vapor phase oxydehydration methods heretofore known to the art. The preferred method comprises contacting a Dawson structure phosphomolybdic acid catalyst with isobutyric acid under specified reaction conditions to achieve a high selectivity for methacrylic acid.

7 Claims, 1 Drawing Figure

HIGH SELECTIVITY PROCESS FOR VAPOR PHASE OXYDEHYDROGENATION OF ALKANOIC ACIDS, SUCH AS ISOBUTYRIC ACID, USING DAWSON STRUCTURE PHOSPHOMOLYBDIC ACID

CROSS-REFERENCE TO RELATED PATENT APPLICATIONS

The present application is related to U.S. patent application Ser. No. 258,102, filed of even date, entitled "Vanadotungstomolybdophosphoric Acid Oxidation Catalyst", now abandoned and to application Ser. No. 257,675, filed of even date, entitled "Oxidation of Isobutylene Oxide To Methacrylic Acid And Methacrolein", now abandoned which applications are assigned to the assignee of the present application, and which are hereby incorporated by reference as if fully set forth herein.

BACKGROUND OF THE INVENTION

The present invention relates generally to the field of syntheses of alpha-beta unsaturated acids, such as methacrylic acid, from saturated acids, such as isobutyric acid, and more particularly to syntheses of such materials using molybdophosphoric acid catalysts.

Methacrylic acid and methacrolein are chemical species which are fundamental to the plastics industry. Methacrylic species such as methacrylic esters, are used in huge quantities worldwide for diverse employment in the elaboration and formulation of structural, coating, aesthetic and other polymerizable resin systems. Accordingly, the efficient synthesis of methacrylic acid and methacrylic precursors such as methacrolein is greatly desired.

Isobutyric acid is a readily available material having the requisite carbon atom structure for transformation into methacrylic acid. Such transformation, however, requires both oxidation and dehydration. Accordingly, catalytic agents which accomplish this transformation in a selective and efficient manner are highly desired.

Heteropolyacids are a recognized class of acids containing large amounts of oxygen and hydrogen, and multiple atoms of one or more elements, such as molybdenum or tungsten, surrounding one or more heteroatoms of another element, such as phosphorous. Polyanions of such acids consist primarily of octahedral $MoO_6$ or $WO_6$ groups, so that the conversion of $[MoO_4]^{2-}$ or $[WO_4]^{2-}$ into polyanions requires an increase in coordination number. Cotton and Wilkinson "Advanced Inorganic Chemistry", 4th edition, pp. 852–861 Wiley & Sons, N.Y. (1980), disclose that heteropolyanions can be formed either by acidification of solutions containing the requisite simple anions, or by introduction of the hetero element after first acidifying the molybdate or tungstate. As indicated at Table 22-C-2 of Cotton and Wilkinson (pg. 857), various heteropolyanion formula types are known.

Heteropolyacids such as molybdophosphoric acids, are known to exist in the stoichiometry of the "Keggin" structure ($PMo_{12}O_{40}^{3-}$), as well as in the stoichiometry of a Dawson structure ($P_2Mo_{18}O_{62}^{6-}$). Of these structures, the "Keggin" structure is the most commonly formed cluster, and Keggin structure molybdophosphoric acids are known to be suitable vapor phase catalysts in the oxidative dehydrogenation of isobutyric acid to methacrylic acid. In Japanese Patent Disclosure Number 1975-4014 dated Jan. 16, 1975 entitled "A Process for Manufacturing Methacrylic Acid, abstracted at *Chemical Abstracts,* Volume 83, 4408b (1975), the use of molybdophosphoric acid having the empirical formula $H_3Mo_{12}PO_{40} \cdot nH_2O$, as well as molybdovanadophosphoric acid, are disclosed for use in vapor phase oxidative dehydrogenations of isobutyric acid. Such reactions are performed in the presence of oxygen and other gases such as nitrogen, steam, etc., such reactions being carried out in the temperature range of 200°–400° C., preferably 250°–350° C. More particularly, this Japanese patent disclosure indicates that the selectivity of methacrylic acid can be improved by using a catalyst which is prepared by adding a sulfate of an alkali metal, nickel or cobalt to a heteropolyacid.

It has long been known to use various heteropolyacids to catalyze certain organic reactions. For example, in U.S. Pat. No. 4,192,951, vapor phase oxidation procedures are disclosed utilizing various heteropolyacid catalysts, including heteropolymolybdic catalysts containing vanadium, tungsten, tantalum or niobium. Such compounds act as catalysts for the synthesis of materials such as maleic acid and acetic acid. U.S. Pat. No. 4,192,951, also discloses a molybdophosphoric acid catalyst having an empirical formula of $H_6[P_2Mo_{18}O_{62}]$ which was prepared using a procedure involving the refluxing of $Mo_3$ and $H_3PO_4$ overnight to produce a bright yellow filtrate. Although the empirical formula provided relating to the molybdophosphoric acid catalyst of the '951 disclosure corresponds to the empirical formula of a Dawson structure catalyst, no mention is made in the '951 patent of the stoichiometry of the structure obtained in Example 1. It is clear from the filtrate color reported in the '951 patent that the stoichiometry of the '951 catalyst is not of the "Dawson" type. In an article entitled "Contribution To The Chemistry of Phosphomolybdic Acids, Phosphotungstic Acids, and Allied Substances", by Hsein Wu, *J. Biol. Chem.,* 43, 189 (1920) a proper procedure for preparing phospho-18-molybdic acid of the Dawson structure is disclosed. As explained by Wu at pages 196 and 197, care must be taken during the preparation of such an acid to avoid the formation of yellow crystals and to obtain orange crystals which are indicative of phospho-18-molybdic acid of the Dawson structure.

In U.S. Pat. No. 4,146,574 entitled "Process For Preparing Heteropolyacids", various heteropoly-acids suitable as components in certain oxidation reactions are disclosed. Such catalysts are described as facilitating the oxidative dehydrogenation of isobutyric acid to methacrylic acid, the oxidative dehydrogenation of methyl isobutyrate to methyl methacrylate and methacrylic acid, the oxidative dehydrogenation of isobutyraldehyde to methacrolein and methacrylic acid, the oxidation of methacrolein to methacrylic acid, and the oxidative dehydrogenation of methylisopropyl ketone to methylisopropenyl ketone. Typically, catalytic reactions of the type disclosed in U.S. Pat. No. 4,146,574 are conducted using a mixture of gases, such as steam, oxygen, and nitrogen which are permitted to contact a catalytic substrate for preselected contact times at preselected reaction temperatures.

While the above-described methods for converting isobutyric acid to methacrylic acid have achieved some success, a need still exists for methods for efficiently and selectively converting isobutyric acid to methacrylic acid.

SUMMARY OF THE INVENTION

The present invention provides an improved method for preparing an alpha-beta unsaturated alkanoic acid from its saturated counterpart using a direct oxydehydrogenation vapor phase synthesis which is catalyzed by a phosphomolybdic acid. Quite surprisingly, it has been found that alkanoic acid conversion and alpha-beta double bond selectivity are increased when a Dawson structure catalyst instead of a Keggin structure catalyst is utilized to catalyze the subject conversion.

Accordingly, the primary object of the present invention is a provision of a direct, phosphomolybdic acid catalyzed synthesis of alpha-beta unsaturated acids, such as methacrylic acid, which synthesis exhibits improved selectivity.

A further object of the present invention is the provision of such a process exhibiting improved percentages of conversion of isobutyric acid.

These, and other objects of the present invention will become apparent from the following, more detailed description.

DETAILED DESCRIPTION OF THE DRAWINGS

Figure 1:
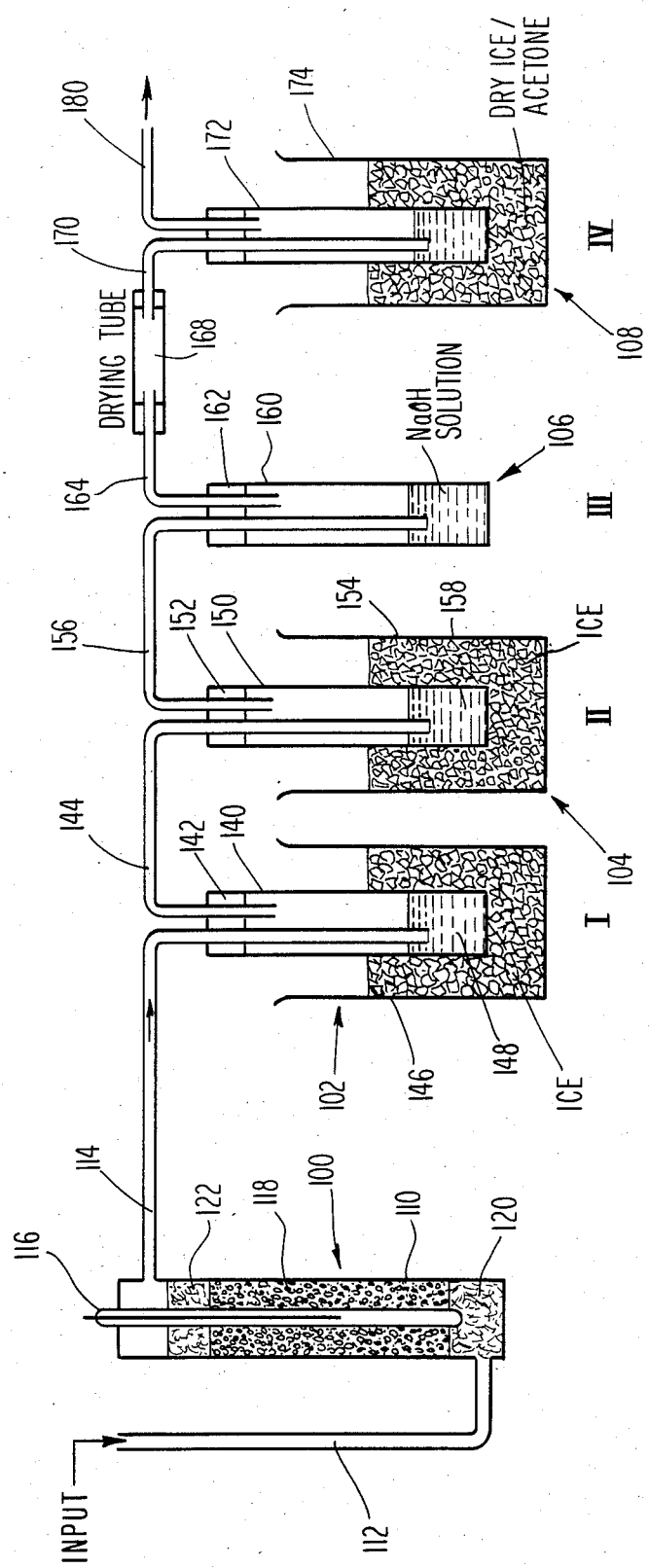

FIG. 1 is a diagrammatic view of the preferred laboratory apparatus for conducting the oxidative dehydrogenation of isobutyric acid in accordance with the present invention.

DESCRIPTION OF THE PREFERRED EMBODIMENTS

While specific examples are described in connection with the following description, one of ordinary skill in the art will recognize that various departures may be made from the materials and methods described herein without departing from the scope of the present invention, which is defined more particularly in the appended claims. As used herein, the term "heteropolyacids" refers to heteropolyacids and their salts, including heteropolyacids having Keggin and Dawson structures, as well as organoheteropoly anions and heteropoly blues, as described in the aforementioned Cotton and Wilkinson text. As used herein, the terms "Dawson structure" and "Dawson cluster" refer to the stoichiometry characterized by the structure $[(X^{+n})_2M_{18}O_{62}]^{(16-2n)-}$ion, the stoichiometry of which is illustrated at FIG. 22-C-6 of "Advanced Inorganic Chemistry", Cotton and Wilkinson, 4th Edition, pages 852–861, Wiley & Sons, New York (1980), which is specifically incorporated by reference as if fully set forth herein.

As used herein the terms "Keggin structure" and "Keggin cluster" refer to ions of the general formula $[X^{+n}M_{12}O_{40}]^{(8-n)-}$ which is also represented at FIG. 22-C-6 of the aforementioned Cotton and Wilkinson publication, and to the various modifications of the Keggin structure and "isomeric" structures referred to in that publication.

The present invention provides a novel method for synthesizing methacrylic acid from isobutyric acid by utilizing molybdophosphoric acid having a Dawson structure rather than a Keggin structure. Accordingly, a Dawson structure phosphomolybdic acid catalyst was prepared in accordance with the above-mentioned method of Wu, as follows: 100 g of $Na_2MoO_4 \cdot 2H_2O$ was dissolved in 450ml of water, and 15ml of 85% $H_3PO_4$ and 80 ml of concentrated HCl were added. The resulting yellow solution was boiled for 24 hours with a reflux condenser. The solution was cooled and 100 g of $NH_4Cl$ was added to give a greenish-yellow precipitate which was filtered and redissolved into an equal weight of water. The ammonium salt of the $PMo_{12}O_{40}^{3-}$ anion, which has a lower solubility than that of the $P_2Mo_{18}O_{62}^{6-}$ anion, can be removed by filtration. To the perfectly clear solution, enough $NH_4Cl$ was added to make a 20% solution. After standing for four hours, the crystalline product was filtered off and recrystallized by dissolving in just enough water and evaporating at a low temperature (40° C.) in a vacuum.

50 g of the recrystallized ammonium salt was dissolved in 100 ml of water with 60 ml of concentrated HCl; and then extracted with ether in a separatory funnel. The bottom layer was diluted with 100 ml of water, 60 ml of concentrated HCl, and extracted with ether. The bottom layer, a clear, orange (which at some times may appear brownish-yellow) ethereal solution was diluted with 40 ml of water and allowed to stand at room temperature; the acid salt crystallized out.

This crystallized acid salt was subjected to elemental analysis, infrared spectroscopy and X-ray diffraction analysis to ensure a Dawson structure had been obtained. Elemental analysis (assuming 13 waters of hydration) indicated the subject compound to contain 2.05% phosphorous, 57.29% molybdenum, and 1.32% hydrogen. These values directly correlate to theoretical Dawson structure values of 2.05% phosphorous, 57.16% molybdenum and 1.07% hydrogen. The experimental molybdenum to phosphorous ratio of 9.02 (theoretical Dawson ratio equals 9.0, theoretical Keggin ratio equals 12.0) also confirms that a nearly pure Dawson structure material was obtained. This conclusion was further confirmed by the infrared spectrum, which produced characteristic adsorption bands at 1080, 950, 890 and 750 cm$^{-1}$ and by X-ray diffraction measurements of the microcrystalline product which showed strong characteristic peaks at two theta values of 8.0, 9.0, 9.9, 24.5, 25.4 and 27.1 degrees.

In order to deposit the catalyst on a catalytic substrate, the hydrated $H_6P_2Mo_{18}O_{62}$ acid salt was first dissolved in water to give a clear, dark orange solution. Silica substrate, such as a colloidal silica sold under the tradename, "Ludox AS", was added to this heteropolyacid solution. The solution was evaporated on a hot plate with vigorous stirring until a cake formed. The solidified catalyst was calcined overnight at 280° C. in an automatic furnace with a constant flow of air. Finally, the 20/50 mesh size calcined catalyst was separated out using a sieve shaker.

The preferred catalyst of the present invention is prepared using a silica substrate sold by the Johns-Manville Company, Denver, Colo. under the tradename "Celite 408". An aqueous solution of known heteropolyacid concentration is absorbed into the silica substrate, and permitted to air dry prior to its use as a catalyst. The aforementioned oven drying and calcining are not believed to be necessary in the preparation of this catalyst. However, it should be noted that processing temperatures are such that drying of the catalyst is assured.

Referring now to FIG. 1, a laboratory scale apparatus for use in performing the method of the present invention is illustrated. This apparatus comprises a reactor designated generally 100 and a series of collection traps designated generally 102, 104, 106 and 108. Reactor 100 comprises a glass reactor vessel 110 which is fed through side arm 112 and which exhausts through output conduit 114. This reactor is fitted with an axially disposed thermometer well 116. Reactor vessel 110 contains a catalyst bed 118 located within the reactor flow stream between glass bead packings 120 and 122. In a preferred embodiment, the catalyst bed comprises 50% heteropolyacid deposited on a suitable silica substrate, such as Celite 408 silica which is sold by the Johns-Manville Company. During use, the reactor is submerged in a salt bath (not shown) filled with 60% $ZnCl_2$, 20% NaCl, and 20% KCl, heated to the desired temperatures. An Isco pump model 314 was used to feed a premixed aqueous isobutyric acid solution to a pre-heater where the liquid feed was vaporized and passed on to the catalyst bed. Oxygen and nitrogen were simultaneously fed into the reactor using a flow meter, model 10A1460, which may be obtained from Fisher and Porter.

The reaction products produced in reactor 100 were collected in the recovery train comprising traps 102, 104, 106 and 108. Condensation trap 102 comprises collection vessel 140 containing a dual port stopper 142 for receiving conduit 114 and tube 144 which are journaled therethough. Collection vessel 140 is partially immersed in ice contained within beaker 146. Reaction products 148 are thus collected by condensation within collecting vessel 140. Those products which do not condense as liquids within reaction vessel 140 are passed through tube 144 to collection trap 104, which similarly comprises collection vessel 150, stopper 152 and ice water container 154 for further fascilitating the collection of condensed reaction products 158.

As shown in FIG. 1, gaseous products not collected in trap 104 pass through conduit 156 to carbon dioxide collection trap 106. Carbon dioxide collection trap 106 similarly comprises a collection vessel 160 fitted with a dual apertured rubber stopper 162. Collection vessel 160 contains a sodium hydroxide solution for collecting carbon dioxide, the amount of which can be subsequently determined by back titrating with an acid. After passing through output tube 164 to a drying tube 168 for removing water vapor from the process stream, the stream is fed through input tube 170 to the collection vessel 172 of volatile products trap 108. Volatile products trap 108 further comprises a container 174 which holds a dry ice/acetone bath in which at least a portion of collection vessel 172 is immersed. The process stream is then vented through exhaust tube 180.

Total acids (isobutyric acid, acetic acid and methacrylic acid) recovered from traps 1 and 2 were then determined by titrating the aqueous solutions with 0.10 M NaOH using phenolphthalein as the indicator. As mentioned above, carbon dioxide collected in trap III (106) was determined by back titration such as with 0.10 N HCl. The reaction products collected by traps 1 and 2 were further subjected to gas chromatographic analysis to determine the percent conversion and, where appropriate, the percent selectivity of the reaction. Gas chromatographic analysis was also used to determine carbon dioxide, oxygen, and, where appropriate, carbon monoxide, using $N_2$ as the standard.

As used herein, percent conversion equals the moles of alkanoic acid reacted divided by the moles of alkanoic acid supplied, times 100. As used herein, percent selectivity refers to the number of moles of a given end product recovered divided by the number of moles of starting material reacted, times 100.

The present method is useful in directly converting short chain, preferably branched, alkanoic acids which have at least one hydrogen at each of the alpha and beta carbons thereof to their corresponding alpha-beta unsaturated acid counterparts. Such alkanoic acids preferably have hydrocarbyl groups at the alpha and/or beta positions comprising 1–5 carbon atoms. The preferred acid species for use in the present method is isobutyric acid which is readily and selectively converted to methacrylic acid.

In order to compare the isobutyric acid conversion and methacrylic acid selectivity of Keggin and Dawson catalysts under similar conditions, a series of experimental runs using the above described apparatus were performed, which runs are reported in Table I:

TABLE I*

| RUN | CATALYST | STRUCTURE | IBA CONVERSION | MAA SELECTIVITY | IBA | MAA | ACETONE | HOAc | $CO_2$ | CO |
|---|---|---|---|---|---|---|---|---|---|---|
| 71-58** | $H_3PMo_{12}O_{40}$ | Keggin | 66% | 45% | 33% | 30% | 11% | 1% | 4% | 10% |
| 71-60** | $H_3PMo_{12}O_{40}$ | Keggin | 61% | 44% | 39% | 27% | 9% | 1% | 5% | 9% |
| 71-62** | $H_3PMo_{12}O_{40}$ | Keggin | 66% | 43% | 33% | 28% | 10% | 1% | 5% | 11% |
| 71-82** | $H_6P_2Mo_{18}O_{62}$ | Dawson | 73% | 53% | 27% | 39% | 13% | 1% | 5% | 11% |
| 71-84** | $H_6P_2Mo_{18}O_{62}$ | Dawson | 70% | 53% | 30% | 37% | 11% | 1% | 4% | 12% |
| 71-80** | $H_6P_2Mo_{18}O_{62}$ | Dawson | 72% | 50% | 28% | 36% | 11% | 1% | 5% | 11% |

*$IBA/H_2O/O_2/N_2 = 1/2/6/24$ (moles); contact time 1 second, bath temperature −280° C.; Sample Collection Time: 2–3 hours; all percents are percents of carbon content of substrate.
**50% heteropolyacid/Celite catalyst.

As seen from Table I, each of the catalysts was run in a bath maintained at 280° C. Proportions of isobutyric acid, water, oxygen and nitrogen were as indicated in the table. By comparing the percent IBA conversion obtained for the catalyst having the Dawson structure versus that having the Keggin structure, it will be noted that the Dawson catalyst produced percent conversions of between 70–73% while the Keggin catalysts produced 61–66% IBA conversions. MAA selectivity was similarly increased, ranging between 50–53% for the Dawson catalyst as opposed to 43–45% for the Keggin catalysts. Accordingly, it will be seen that the Dawson catalyst is superior in both percent conversion of IBA and selectivity of MAA over the tested Keggin structures.

In Japanese patent publication 75-04,014 (Kokai) Mitsubishi reports a 45% MAA selectivity for a similar Keggin catalyst. Mitsubishi's results are, however, not directly comparable due to different feed ratios. (IBA-/$O_2$/N = 1/1/33), a different temperature (265° C.) and a 3.6 second contact time which resulted in an 82% conversion. The results for the Dawson catalyst set forth in Table I nonetheless compare favorably to Mitsubishi's results.

It should be noted that the above described results utilize the aforementioned heteropolyacids/celite catalyst. Experimental results have indicated that the Ludox support is not well adapted to supporting the catalysts described herein, and will result in very significant reductions in the percent conversions obtained if used in the practice of the present invention.

From the foregoing description, one of ordinary skill in the art will recognize that the reaction of the present invention should be conducted at sufficient temperatures to facilitate the conversion of the subject substrate to the desired end product(s), but below the temperature at which substantial decomposition of the subject catalyst occurs, generally between about 260° C. and 330° C. For example, at atmospheric pressures, the temperature of the bath in which the catalyst is contained should be maintained between about 280°–350° C., and more preferably between 285°–335° C. Additionally, the subject reactions may be run at pressures between 5–50 psig, preferably 10–30 psig. It is also preferred to use an inert diluent gas to bring the system up to proper operating pressures and to otherwise maintain favorable reaction conditions. Such inert diluents include any gas which is otherwise inert to the system, including, for example, argon, helium, nitrogen, carbon dioxide and excess steam. In any event, the subject reactions should be run with enough steam to stabilize the catalyst by, for example, maintaining the hydration of the catalyst. Contact time of the substrate with the catalyst should be controlled to achieve optimum percentages of conversion at desired selectivities. Such contact times typically range between 0.1–10 seconds preferably between 0.5–5 seconds. In performing the subject reactions, sufficient oxygen should be introduced to accomplish the desired oxidation. Generally, 0.1–25, preferably 1–12, molar equivalents of oxygen per mole of substrate should be introduced with the substrate to carry out the subject oxidation. One of ordinary skill will further recognize that various catalyst supports other than silica may be used with the disclosed catalyst. See for example, U.S. Pat. No. 4,146,574, column 3, lines 47–66, which patent is hereby incorporated by reference.

As seen from the above, the present invention provides a simple, direct, high conversion method for converting an alkanoic acid such as isobutyric acid to its corresponding alpha-beta unsaturated counterpart which method exhibits a substantially higher degree of selectivity than heretofore known to the art.

We claim:

1. A method for producing an alpha-beta unsaturated acid, comprising the steps of:
   (a) providing an alkanoic acid having at least one hydrogen atom attached to each of the alpha and beta carbons thereof;
   (b) providing a catalyst comprising a Dawson cluster phosphomolybdic acid;
   (c) contacting said catalyst at a temperature between 260° C. and the temperature at which substantial decomposition of said catalyst occurs with a reaction gas comprising said alkanoic acid, water and oxygen to convert at least a portion of said alkanoic acid into a reaction product comprising its corresponding alpha-beta unsaturated alkanoic acid.

2. The method of claim 1 wherein said alkanoic acid of step (a) is isobutyric acid.

3. The method of claim 1 wherein said reaction gas comprises an inert diluent gas.

4. The method of claim 1 wherein said method is performed at temperature between 260° and 330° C.

5. The method of claim 4 wherein said method is performed at about 280° C.

6. The process of claim 2 wherein said catalyst is deposited on a substrate, as carrier.

7. The method of claim 6 wherein said substrate is silica.

* * * * *